United States Patent
Borot et al.

(10) Patent No.: US 11,029,400 B2
(45) Date of Patent: Jun. 8, 2021

(54) METHODS AND SYSTEM FOR MAINTAINING POLARIZATION OF AN ULTRASOUND TRANSDUCER

(71) Applicant: General Electric Company, Schenectady, NY (US)

(72) Inventors: Maxence Borot, Nice (FR); Alan Tai, Phoenix, AZ (US); Edouard dacruz, Nice (FR); Flavien Daloz, Antibes (FR); Fan Zheng, Tempe, AZ (US); Jeremie Barrel, Opio (FR); Frederic Lanteri, Le Cannet (FR)

(73) Assignee: General Electric Company, Schenectady, NY (US)

( * ) Notice: Subject to any disclaimer, the term of this patent is extended or adjusted under 35 U.S.C. 154(b) by 388 days.

(21) Appl. No.: 16/043,003

(22) Filed: Jul. 23, 2018

(65) Prior Publication Data
US 2020/0025897 A1    Jan. 23, 2020

(51) Int. Cl.
| G01S 7/52 | (2006.01) |
| A61B 8/00 | (2006.01) |
| A61B 8/08 | (2006.01) |
| A61B 8/14 | (2006.01) |

(52) U.S. Cl.
CPC .......... *G01S 7/52046* (2013.01); *A61B 8/14* (2013.01); *A61B 8/461* (2013.01); *A61B 8/5246* (2013.01); *A61B 8/5269* (2013.01); *G01S 7/5202* (2013.01)

(58) Field of Classification Search
CPC ............... G01S 7/52046; G01S 7/5202; G01S 7/52004; G01S 15/8915; G01S 7/52085; A61B 8/5269; A61B 8/14; A61B 8/461; A61B 8/5246; A61B 8/483; A61B 8/486; A61B 8/488; A61B 8/485; A61B 8/4427; A61B 8/00
See application file for complete search history.

(56) References Cited

U.S. PATENT DOCUMENTS

| | | |
|---|---|---|
| 6,497,660 B1 | 12/2002 | Dillman et al. |
| 2004/0254459 A1 | 12/2004 | Kristoffersen et al. |
| 2008/0200809 A1 | 8/2008 | Shifrin |
| 2014/0018679 A1 | 1/2014 | Chen et al. |
| 2020/0000439 A1* | 1/2020 | Satoh ................ A61B 8/5207 |
| 2020/0025897 A1* | 1/2020 | Borot .................... A61B 8/14 |

FOREIGN PATENT DOCUMENTS

| | | |
|---|---|---|
| EP | 1881347 A1 | 1/2008 |
| EP | 2781929 A2 | 9/2014 |
| JP | 2018-124632  * | 1/2020 |
| WO | 2017002007 A1 | 1/2017 |

* cited by examiner

*Primary Examiner* — Daniel Pihulic
(74) *Attorney, Agent, or Firm* — McCoy Russell LLP (57) ABSTRACT

Various methods and systems are provided for maintaining polarization of an ultrasound probe and increasing image quality of an image generated during an imaging procedure. As one example, a method for an ultrasound imaging system may include executing one or more imaging sequences with an ultrasound transducer; and applying a repolarization sequence to the ultrasound transducer one or more of before, after, and interleaved between the one or more imaging sequences, where the repolarization sequence is separate from the one or more imaging sequences.

15 Claims, 5 Drawing Sheets

METHODS AND SYSTEM FOR MAINTAINING POLARIZATION OF AN ULTRASOUND TRANSDUCER

FIELD

Embodiments of the subject matter disclosed herein relate to ultrasound transducers and ultrasound imaging.

BACKGROUND

Ultrasound, for medical or industrial applications, is an imaging modality that employs ultrasound waves to probe the acoustic properties of a target object (e.g., the body of a patient) and produce a corresponding image. Generation of sound wave pulses and detection of returning echoes is typically accomplished by an ultrasound probe having an array of transducers. Such transducers typically include electromechanical elements capable of converting electrical energy into mechanical energy for transmission of ultrasonic waves into the target object (e.g., patient tissue) and mechanical energy back into electrical energy when the reflected ultrasonic waves reach the transducers.

Ultrasound probes employ ferroelectric materials to generate ultrasound acoustic energy. As one example of such ultrasound probes, the transducer elements of the probe may be piezoelectric transducer elements that mechanically vibrate when driven by a high voltage signal and convert vibrations due to received echo signals into electrical signals. These piezoelectric elements may be made of a ceramic material, such as PZT or PIN-PMN-PT single crystal which are composed in the natural state of microscopic electric dipoles which have random orientation rendering the overall polarization of the material zero. As a result of the randomly oriented dipoles, the piezoelectric elements have a weak piezoelectric effect. To activate the full piezoelectric potential of the material, the electric dipoles should be aligned in one direction. This process of forcing the dipoles to orient themselves in a prescribed direction is called poling and is generated by applying a strong electric field in the intended direction for a threshold amount of time. The reversal of the overall polarization after the initial poling is called depolarization. Depolarization occurs when ferroelectric materials are subjected to either high temperatures, a high mechanical pressure, or a high electric field with a polarity opposite to the polarity of the electric dipoles of the ferroelectric materials.

BRIEF DESCRIPTION

In one embodiment, a method comprises executing one or more imaging sequences with an ultrasound transducer; and applying a repolarization sequence to the ultrasound transducer one or more of before, after, and interleaved between the one or more imaging sequences, where the repolarization sequence is separate from the one or more imaging sequences.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of repolarizing and increasing a sensitivity of an ultrasound transducer (e.g., probe). Ultrasound transducers are included in an ultrasound imaging system, such as the ultrasound imaging system shown in FIG. 1. While performing imaging, via transmitting one or more imaging transmit pulse sequences, the ultrasound transducer may be subjected to high voltages. When exceeding a voltage pulse threshold, the transducer elements of the ultrasound probe become depolarized, which may lead to the degradation of image quality due to a drop of sensitivity. This happens when the voltage of the imaging transmit pulses applied to the ultrasound transducer have a polarity opposite to the polarity of the electric dipoles of the ferroelectric materials of the transducer elements. In order to overcome the issues with depolarization of transducer probes during use, the transducer probes may be repolarized directly before, after, or during an imaging operation. For example, as shown in the example graphs of FIGS. 2-3, one or more repolarization sequences, which include transmit pulses adapted for repolarization of the transducer elements of the ultrasound probe, may be applied to one or several channels of the ultrasound transducer either before, after, or interleaved between imaging sequences, which include transmit pulses adapted for imaging. The repolarization sequences may be triggered manually by a user, automatically at set intervals, or automatically based on a sensitivity of the ultrasound probe, as illustrated by the example method of FIG. 4 and example graph of FIG. 5. In this way, a sensitivity and efficiency of the ultrasound transducer may be maintained and/or enhanced, thereby increasing image quality produced by the ultrasound system. Further, depolarization of the ultrasound transducer may be reduced by regularly applying the repolarization sequence(s) before, after, or interleaved between imaging sequences.

Figure 1:
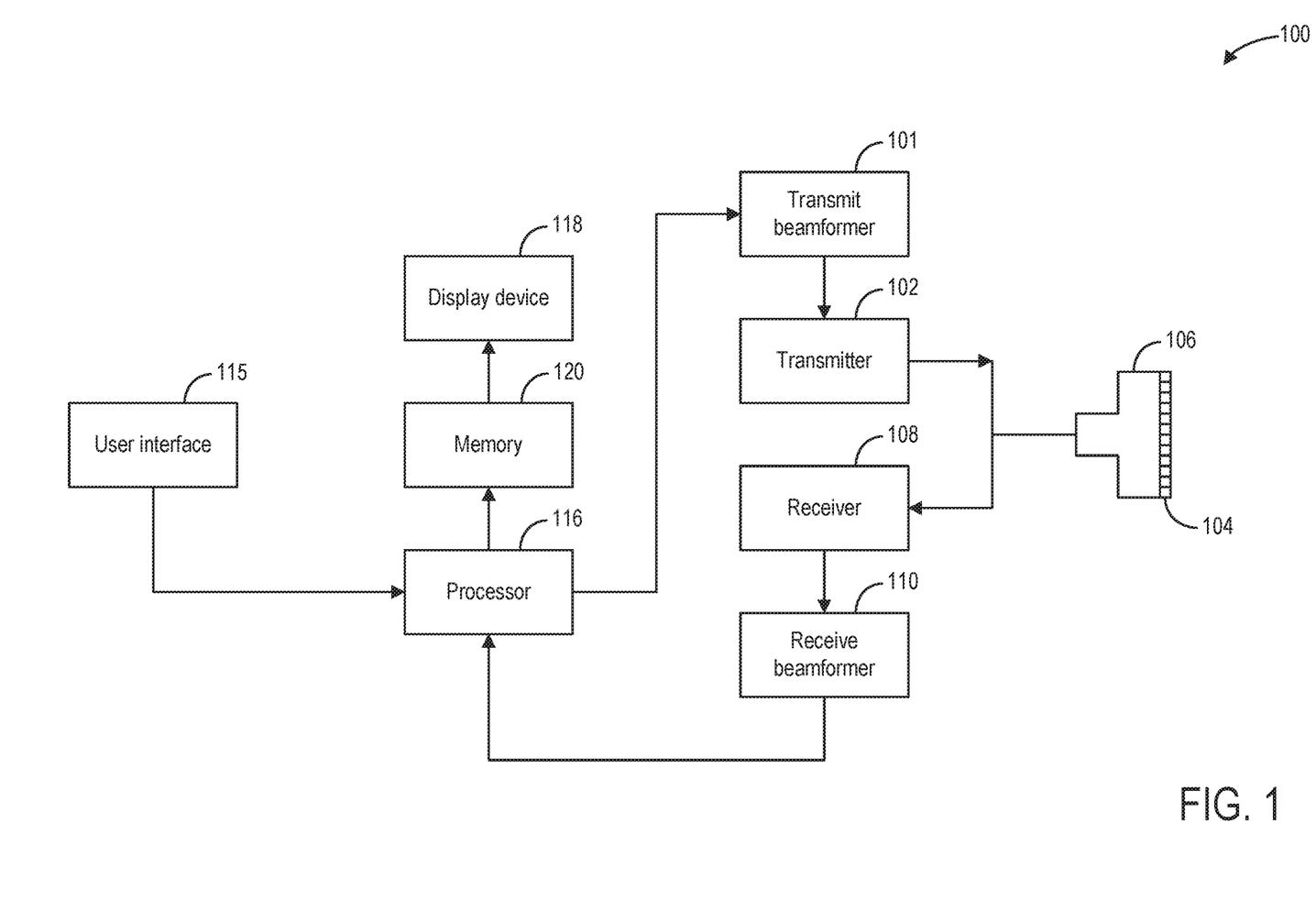
FIG. 1 shows an example ultrasound imaging system according to an embodiment of the invention.

Turning now to FIG. 1, a schematic diagram of an ultrasound imaging system 100 in accordance with an embodiment of the invention is seen. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

The elements 104 of the probe may be made of ferroelectric materials, such as piezoelectric ceramic material such as PZT, PMN-PT, PZN-PT, and PIN-PMN-PT single crystal. Ferroelectric materials possess a spontaneous electric polarization that can be reversed by the application of an external electric field. Piezoelectric ceramic materials are composed in the natural state of microscopic electric dipoles which have random orientation rendering the overall polarization of the material zero and hence a relatively weak piezoelectric effect. To activate the full piezoelectric potential of the material, the electric dipoles should be aligned in one direction. This process of forcing the dipoles to orient themselves in a prescribed direction is called poling and is performed by applying a strong electric field in the intended direction for a sufficient time. However, during imaging (applying imaging sequences with an ultrasound probe), the material of the probe transducer elements may be depolarized. Specifically, this may occur when the imaging pulse sequence with a polarity opposite to the initial polarization direction of the ferroelectric material, reaches a threshold amplitude called a ceiling voltage. The depolarization of the piezoelectric material induces a decrease in sensitivity of the ultrasound probe over time resulting in the degradation of the imaging quality.

In order to maintain the polarization and sensitivity of the ultrasound probe, the transducer elements of the probe may be repolarized, either before, after, or during the transducer operation (e.g., a repolarization sequence could be interleaved between imaging sequences with the probe). Specifically, as explained further below with reference to FIGS. 2-5, in order to image an object (such as tissue of a patient), one or more imaging sequences of transmit pulses may be applied to elements of an ultrasound transducer. These transmit signals of the imaging sequences may be adapted for imaging (e.g., for sending sound waves into the object to be imaged and receiving echo signals used to generate an image of the object). In order to reduce depolarization of the probe and maintain a sensitivity of the probe, a repolarization sequence of transmit pulses, different from the transmit pulses of the imaging sequences, may be applied to the ultrasound transducer. These transmit signals of the repolarization sequence may be adapted for repolarizing the transducer (and not imaging). For example, the repolarization transmit pulse sequence may include pulses that have an average voltage that is in a same direction (positive or negative) of a polarity of the ferroelectric material of the transducer elements, as explained further below with reference to FIG. 2. The repolarization sequence is separate from the imaging sequence and may be applied before, after, or interleaved between imaging sequences, as explained further below with reference to FIG. 3. This arrangement of the repolarization sequence(s) may allow the sensitivity of the ultrasound transducer to stay at an upper threshold level over time, thereby resulting in a more stable ultrasound probe and increasing imaging quality.

Figure 2:
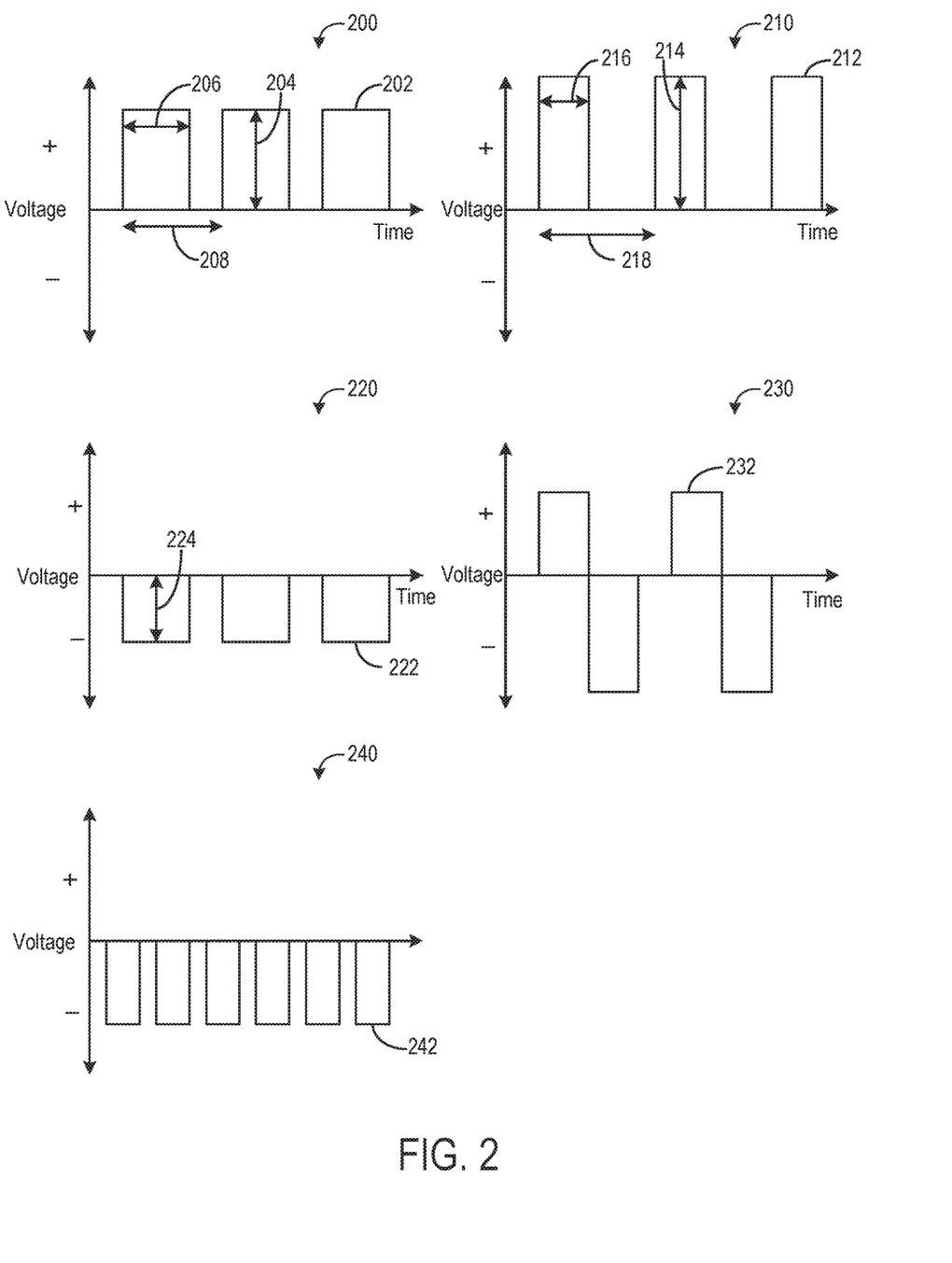
FIG. 2 shows examples of different repolarization transmit pulse sequences that may be applied to an ultrasound probe before, after, or interleaved between imaging transmit pulse sequences, according to an embodiment of the invention

FIG. 2 shows examples of different repolarization transmit pulse sequences that may be applied to the ultrasound probe before, after, or interleaved between imaging transmit pulse sequences. Specifically, FIG. 2 shows a plurality of plots showing different example repolarization sequences that may be used to repolarize or maintain the polarization of an ultrasound probe either before, after, or interleaved between imaging transmit pulse sequences. Each of the plots shown in FIG. 2 include time along the x-axis and voltage (positive or negative) along the y-axis. Each repolarization sequence shown in FIG. 2 has an amplitude, pulse width, frequency, and pulse repetition frequency, PRF (e.g., number of pulses of a repeating signal in a specific time unit, normally measured in pulses per second).

First plot 200 shows a first repolarization sequence 202 with amplitude 204, pulse width 206, and frequency 208. The first repolarization sequence is unipolar with a positive polarity (since the direction of polarity of the ferroelectric material of the ultrasound transducer elements is positive, in this example). Second plot 210 shows a second repolarization sequence 212 with amplitude 214, pulse width 216, and frequency 218. The second repolarization sequence 212 has a larger amplitude 214, smaller pulse width 216, and a lower frequency 218 (with longer time between subsequent pulses) than that of the first repolarization sequence 202. The second repolarization sequence 212 is also unipolar with positive polarity (same direction as polarity of ferroelectric material of the ultrasound transducer elements, in this example). Third plot 220 shows a third repolarization sequence 222 which has a smaller amplitude 224 than the first repolarization sequence 204. Additionally, the third repolarization sequence 222 is unipolar with a negative polarity (since the direction of polarity of the ferroelectric material of the ultrasound transducer elements is negative, in this example). Fourth plot 230 shows a fourth repolarization sequence 232 which is bipolar and asymmetric. Specifically, the negative amplitude of the bipolar pulse of the fourth repolarization sequence 232 is greater than the positive amplitude of the bipolar pulse (since the direction of polarity of the ferroelectric material of the ultrasound transducer elements is negative, in this example). Thus, the mean amplitude of the fourth repolarization sequence 232 is negative and non-zero. In alternate embodiments, the repolarization sequence may be bipolar, similar to repolarization sequence 232, but symmetric (e.g., symmetric across the x-axis so that the mean amplitude of the pulse is zero). In this embodiment, the symmetric repolarization sequence may maintain the repolarization (but may not repolarize after being depolarized). Fifth plot 240 shows a fifth repolarization sequence 242 that is unipolar with negative polarity. However, the frequency and pulse repetition frequency (PRF) of the fifth repolarization sequence 242 is higher than the other examples shown in FIG. 2.

Figure 3:
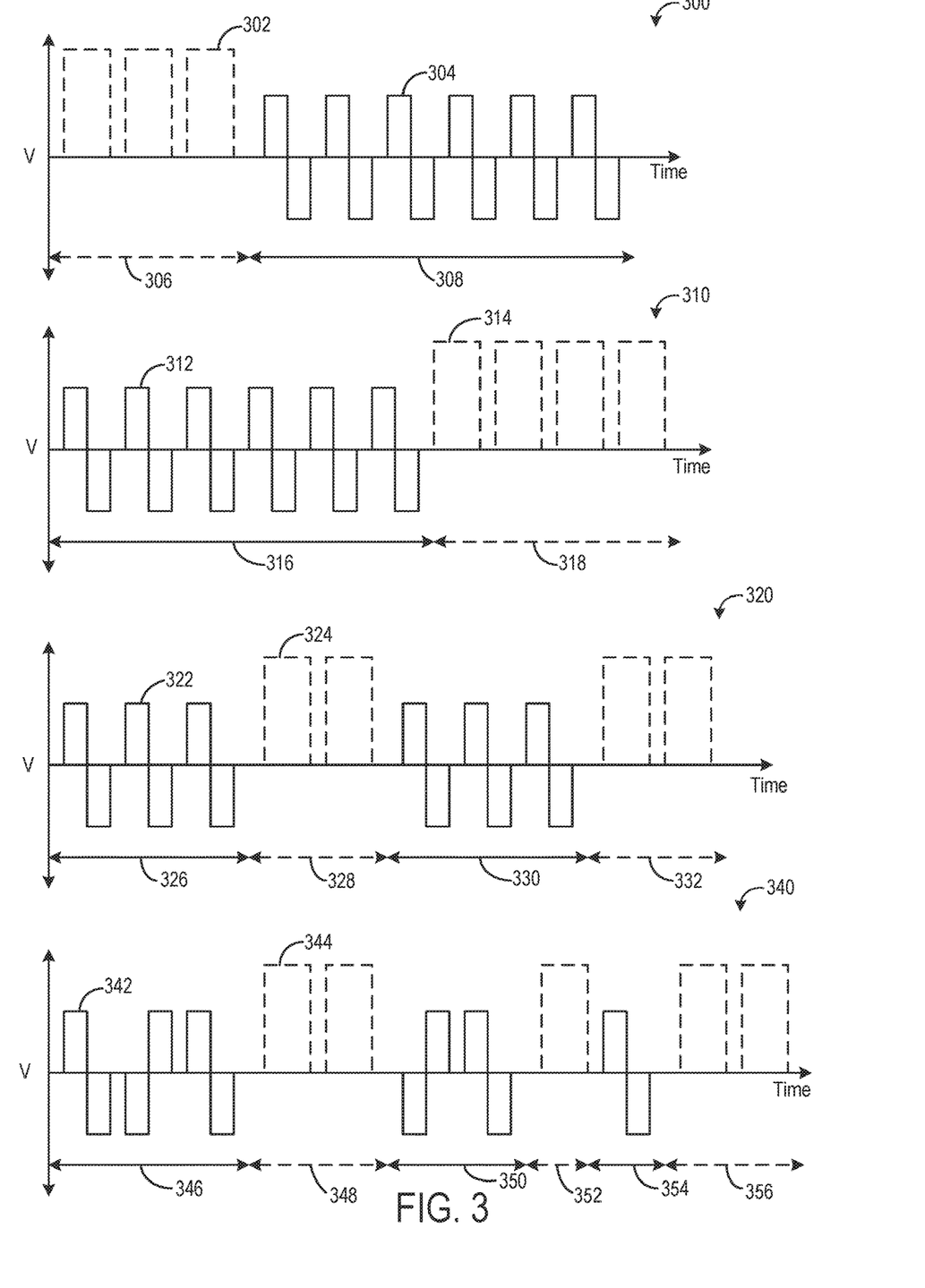
FIG. 3 shows example timeline graphs of imaging and repolarization sequences applied to an ultrasound probe, according to an embodiment of the invention.

FIG. 3 shows example timeline graphs of imaging and repolarization sequences applied to an ultrasound probe, such as the probe 106 shown in FIG. 1. Though the graphs in FIG. 3 all show repolarization sequences with a same, unipolar, positive polarity repolarization transmit pulse, different repolarization sequence transmit pulses may be used in place of those shown in FIG. 3 (such as any of the transmit pulses of the repolarization sequences shown in FIG. 2, or another repolarization transmit pulse sequence with different combinations of amplitude, frequency, PRF, polarity, and pulse width). Each graph of FIG. 3 shows time on the x-axis and voltage (positive and negative) on the y-axis.

Specifically, FIG. 3 shows a first graph 300 illustrating an example of applying a repolarization sequence 302 to an ultrasound probe directly before applying an imaging sequence 304 to the ultrasound probe. Graph 300 shows a duration 306 of applying the repolarization sequence 302 which is shorter than a duration 308 of applying the imaging sequence 304. In alternate embodiments, the durations 306 and 308 may be longer or shorter than those shown in graph 300. In this way, a repolarization sequence may be applied directly before applying an imaging sequence, without any additional events occurring between the application of the repolarization sequence and imaging sequence.

FIG. 3 also shows a second graph 310 illustrating an example of applying a repolarization sequence 314 to an ultrasound probe directly after applying an imaging sequence 312 to the ultrasound probe. In the example of graph 310, the duration 318 of the repolarization sequence 314 is shorter than the duration 316 of the imaging sequence. The duration 318 may be shorter or longer in alternate embodiments. In some examples, the duration 318 of the repolarization sequence 314 may be based on a constant times the duration 316 of the imaging sequence 312. For example, the repolarization sequence 314 may have ⅔ the number of transmit pulses as the imaging sequence 312. Additionally, the imaging sequence 312 shown in graph 310 is an example of a b-mode imaging pulse sequence (however, different types of imaging pulse sequences may be used with the repolarization sequence, such as harmonic pulse sequences, as shown in graph 340).

Graph 320 of FIG. 3 illustrates an example of applying a repolarization sequence 324 interleaved between imaging sequences 322 at regular intervals. Specifically, as shown in graph 320, repolarization sequences 324 of same duration 328 are interleaved between imaging sequences 322 of set duration 326. In one example, a repolarization sequence 324 may be automatically applied to the transducer elements of the ultrasound probe after the duration 326 of applying the imaging sequence 322, which may correspond to a number of imaging pulses (in this example, three bipolar, b-mode pulses). In this embodiment, a set number of repolarization pulses (e.g., 2) are automatically applied to the probe after the conclusion of applying a set number of imaging pulses (e.g., 3). However, in alternate embodiments the set numbers of repolarization and imaging pulses may differ from the example shown in graph 320.

Graph 340 of FIG. 3 illustrates an example of applying a repolarization sequence 344 interleaved between imaging sequences 342 at irregular intervals. In the example shown in graph 340, the transmit pulses of imaging sequences 342 are bipolar, harmonic pulses (alternating polarity pulses). As shown in graph 340, each imaging sequence 342 may have a different duration 346, 350, and 354 (and different number of pulses) and each repolarization sequence 344 may have a different duration 348, 352, and 356 (and different number of pulses). In this way, the repolarization sequences may occur at irregular intervals and for different durations between subsequent imaging sequences. In one example, the duration and times of occurrence of the repolarization sequence may be initiated by one or more of a decrease in sensitivity of the ultrasound probe, a manual user input, or a break in the imaging sequence (e.g., to generate a view an image) and based on a duration of the previous imaging sequence. For example, in one embodiment, as a duration of an imaging sequences increases, a duration of a following repolarization sequence may also increase.

Figure 4:
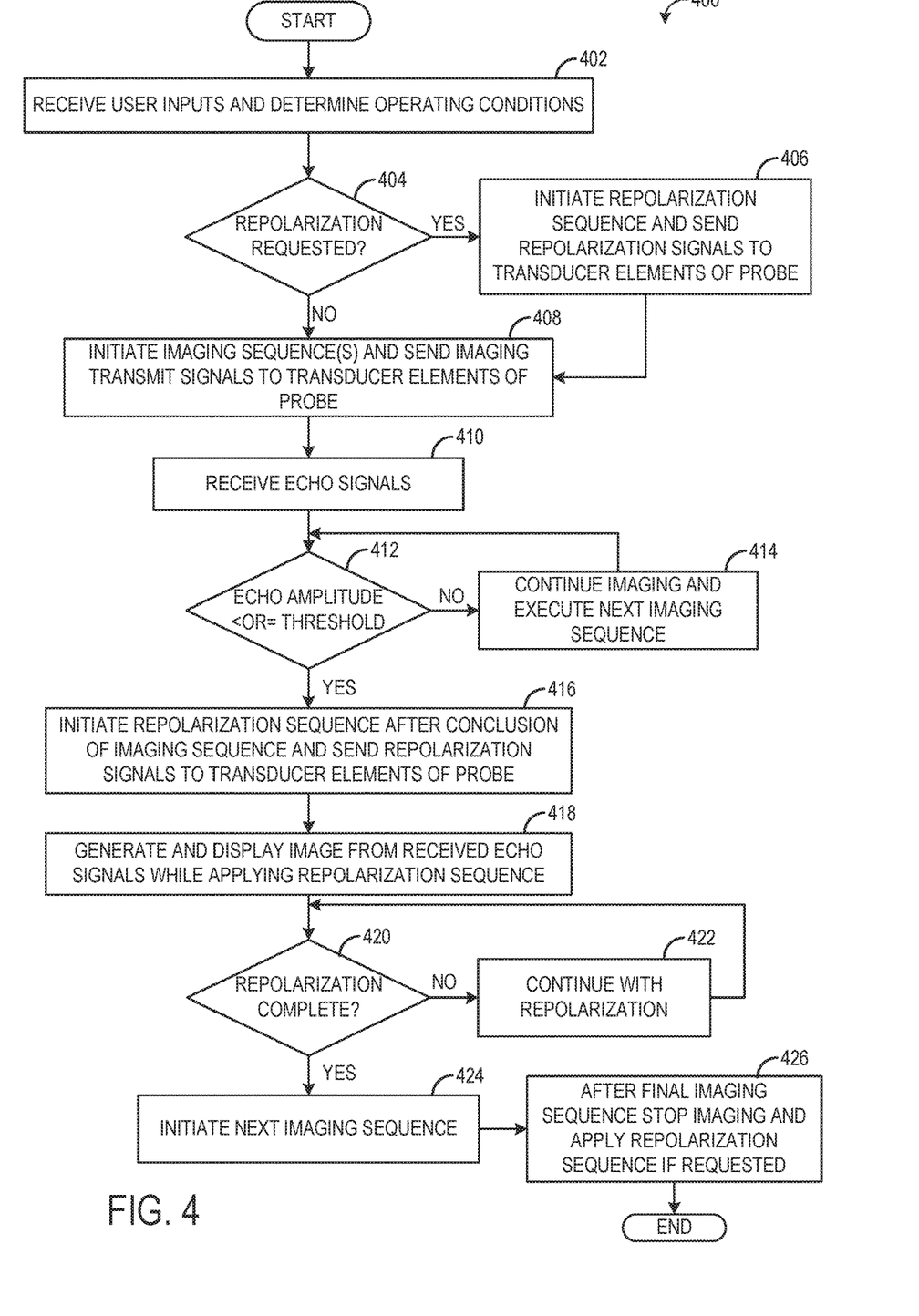
FIG. 4 shows a flow chart of a method for applying repolarization sequences to an ultrasound probe, according to an embodiment of the invention.

Turning now to FIG. 4, a flow chart of a method 400 for applying repolarization sequences to an ultrasound probe is shown. Method 400 may be implemented with an ultrasound system, such as the ultrasound imaging system 100 shown in FIG. 1. Instructions for carrying out method 400 may be executed by a controller or processor of the ultrasound imaging system (e.g., processor 116) based on instructions stored on a memory of the controller or processor and in conjunction with signals received from sensors of the imaging system (such as echoes received by the receiver and receive beamformer, and signals received from the user interface described above with reference to FIG. 1). The controller or processor may employ actuators (such as the transmit beamformer, transmitter, and probe) of the imaging system to adjust imaging system operation, according to the methods described below.

Method 400 begins at 402 by receiving user inputs and determining operating conditions of the imaging system. Receiving user inputs may include receiving inputs from a user interface of the imaging system. User inputs may include an input requesting repolarization of the ultrasound probe, in one example. Additionally, the user inputs requesting the repolarization sequence may specify a duration, frequency, amplitude, pulse width, and/or PRF of transmit pulses of the repolarization sequence and/or specify when in the imaging procedure the repolarization is to occur (e.g., before, after, or interleaved between imaging sequences). In alternate examples, the user inputs may include an input requesting automatic repolarization of the ultrasound probe at set intervals during an imaging procedure, between imaging sequences (e.g., the input may request a repolarization sequence of X pulses or Y duration to occur automatically after A transmit pulses of an imaging sequence or B duration of an imaging sequence). In yet another example, the user inputs may include an input requesting automatic repolarization of the ultrasound probe in response to an echo amplitude being less than a set threshold, where the set threshold is input by a user. In still another example, the user inputs may be include a set repetition time for executing a repolarization sequence.

At 404, the method includes determining whether repolarization of the ultrasound probe is requested. As explained above, repolarization of the ultrasound probe may be requested manually via the controller receiving a user input requesting repolarization. Repolarization may also be requested automatically in response to a set interval for performing the repolarization sequence (e.g., after each imaging sequence, after a predetermined number of imaging sequences, after a user input or predetermined number of imaging transmit pulses, after a duration of imaging with the ultrasound probe, and the like). In another example, repolarization may be set to occur upon startup of the imaging system, before beginning an imaging operation that includes sending imaging transmit pulses to the ultrasound probe that result in ultrasound pulses being sent into an object to be imaged.

If repolarization is requested at 404, either manually or automatically according to predetermined settings, the method continues to 406 to initiate a repolarization sequence and send repolarization signals (e.g., repolarization transmit pulses) to the transducer elements of the ultrasound probe. As one example, sending the repolarization signals may include sending the repolarization signals to one or more channels of the ultrasound transducer (e.g., probe). For example, the method at 404 may include determining (e.g., identifying) which individual elements of the plurality of transducer elements are depolarized (e.g., based on signals from the individual transducer elements). The method may then include sending repolarization signals to only the transducer elements that have been identified as depolarized, in one example. In other examples, the method may include sending repolarization signals to all transducer elements of the probe within predetermined periods. In this way, the repoling pulses can be programmed to be sent to any of the elements of the transducer probe or a group of elements of the transducer probe at the same time for repoling during the non-scanning time or waiting period for the scanning modes of the system, according to predetermined conditions. For example, if it is determined that only a couple of the transducer elements are depolarized, just those identified elements may be repolarized. Alternatively, if it is predicted, based on test data, that all the transducer elements will be depolarized after a period of time, then the method may include repolarizing all the transducer elements at the same time. Moreover, the determination of which elements or element subset to repolarize may be determined either by the user or automatically based on the specific criteria (e.g., a sensitivity threshold, as explained further below).] The repolarization sequence may include one or more repolarization transmit pulses. The number of transmit pulses in the repolarization sequence may be selected by a user (via a user input sent to the controller), predetermined and set in the imaging system, determined based on the number of transmit pulses in an imaging sequence occurring before and/or after the repolarization sequence (e.g., number of repolarization transmit pulses=N*number of imaging transmit pulses occurring before the repolarization sequence, where N is a non-zero, positive value), and/or determined based on a current sensitivity of the ultrasound probe. As one example, the controller may determine the number of repolarization transmit pulses to send to the probe during the repolarization sequence according to logic rules that are a function of the number of imaging transmit pulses in an imaging sequence occurring before the repolarization sequence. In yet another example, the controller may determine the number of repolarization transmit pulses in the repolarization sequence using a look-up table stored in memory of the controller where the number of imaging transmit pulses is the input to the table and the number of repolarization transmit pulses is the output of the table. The repolarization sequence applied at 406 may be any of or similar to the repolarization sequences shown in FIGS. 2 and 3. As discussed above, the pulses of the repolarization sequence may have various amplitudes, pulse widths, frequency, PRF, and the like. These parameters may be pre-set at the controller, selected by a user, and/or automatically selected based on (according to logic rules and/or look-up tables) a sensitivity of the probe and/or characteristics of the imaging sequences. The transmit pulses of the repolarization sequence are adapted for (e.g., optimized for) repolarization of the ultrasound probe. For example, a polarity of the repolarization transmit pulses (e.g., average polarity negative or positive) is selected to be in a same direction as the polarity of the ferroelectric material of the transducer elements of the ultrasound probe. Additionally, while imaging transmit pulses may have a frequency within transducer frequency range, the frequency of repolarization transmit pulses may be selected solely based on the efficiency of the repolarization, where the lower the frequency the more efficient the repolarization. The repolarization transmit pulses may be sent into the body of a patient if the patient is touched by the probe during the repolarization time. However, the signals received by the probe during repolarization (e.g., during sending repolarization transmit pulses to the probe) may not be displayed on the screen of the ultrasound system as the repolarization does not need to be overlapped with the scanning time of the scanning modes. Said another way, no image may be generated from the data generated from sending the repolarization pulses to the probe. Further, initiating the repolarization sequence at 406 may include the controller (or processor) of the imaging system sending command signals to the transmit beamformer (e.g., transmit beamformer 101 shown in FIG. 1), the transmit beamformer forming the repolarization transmit pulses according to the command signals received from the processor, and the transmit beamformer sending these transmit pulses to the transmitter (e.g., transmitter 102 shown in FIG. 1) which transmits the repolarization transmit pulses to the individual transducer elements of the ultrasound probe. The method then continues to 408, as described further below.

Returning to 404, if repolarization is not requested, the method continues to 408 to initiate one or more imaging sequences and send imaging transmit signals to the transducer elements of the ultrasound probe. The imaging transmit signals may include one or more (e.g., a plurality of) imaging transmit pulses which are adapted for (e.g., optimized for imaging). For example, the imaging transmit pulses may include b-mode, harmonic, or alternate types of imaging pulses adapted to send sound waves into an object (e.g., patient tissue) and receive echo signals back which may be used to generate an image of the object. Similar to as described above with reference to 406, the method at 408 may include the controller sending command signals to the transmit beamformer, the transmit beamformer forming the imaging transmit pulses according to the command signals received from the processor, and the transmit beamformer sending these transmit pulses to the transmitter which transmits the imaging transmit pulses to the individual transducer elements of the ultrasound probe, which then results in sound waves being emitted from the ultrasound probe into the object to be imaged.

At 410, the method includes receiving the echo signals via the ultrasound probe, receiver (e.g., receiver 108 shown in FIG. 1), and/or receive beamformer (e.g., receive beamformer 110 shown in FIG. 1). These received echo signals may then be sent to the controller (e.g., processor 116 shown in FIG. 1) for processing and generation of an ultrasound image. The generated image may then be sent to a display device (e.g., display device 118 of FIG. 1) for displaying the generated image to a user.

At 412, the method includes determining whether the amplitude of the received echo signals are less than the threshold. The echo amplitude may correspond to a sensitivity of the ultrasound probe, which may degrade as the transducer elements become depolarized during imaging sequences. Thus, by tracking the sensitivity (via the amplitude of the echo signals, or alternate parameters in another embodiment), it may be detected when repolarization is desired. For example, as the echo amplitudes decrease during imaging, due to transducer element depolarization, the sensitivity of the probe may decrease and image quality of the generated image may degrade. Thus, the echo amplitude threshold at 412 may be a value below which image quality degrades by a set percentage (e.g., 10%, 20%, or 30%) and/or a value below which a threshold percentage of elements of the probe become depolarized (e.g., 40, 50, or 60%). If the echo amplitude of the received echo signals during execution of the imaging sequence(s) is not less than or equal to the threshold, the method continues to 414 to continue imaging (e.g., continue executing the imaging sequence(s) and sending the imaging transmit signals to the probe) and execute the next imaging sequence. The method may then loop back to 412.

Alternatively at 412, if the echo amplitude of the received echo signals during execution of the imaging sequence(s) is at or below the threshold, the method continues to 416 to initiate a repolarization sequence after a conclusion of the imaging sequence and send repolarization signals to the transducer elements of the probe. The method at 416 may proceed similarly to that of 406, as described above. In this way, the repolarization sequence may be automatically initiated responsive to the received echo signals during the imaging sequence, and directly after concluding the imaging sequence. This may result in the repolarization sequence being interleaved between imaging sequences (e.g., if another imaging sequence is initiated after execution of the repolarization sequence, as described further below).

The method at 418 includes generating a displaying an image from the received echo signals while applying the repolarization sequence to the probe at 416. In this way, the methods at 416 and 418 may occur concomitantly with one another. For example, while an image generated from signals received from the executed imaging sequence is being displayed and analyzed by a user, the repolarization sequence may be executed. In this way, the repolarization sequence may occur in a break in the imaging procedure, while the probe is not being used for imaging (and not sending imaging pulses to the probe). For example, whenever a probe is plugged into a system, there is an initiation time where the scanning mode is not yet active and being executed. During this time or break, the repolarization pulses may be sent to the elements of the probe to strengthen the polarization condition of the probe after previous use. Another example of taking advantage of the break time for repolarization is during the "freeze" and "unfreeze" of capturing the image displayed in the screening. Similarly, during this time or break, the repolarization pulses may be sent to the elements of the probe to strengthen the polarization condition of the probe.

The method continues to 420 to determine whether repolarization is complete. Repolarization may be complete after the set or predetermined number of repolarization transmit pulses have been executed (e.g., sent to the ultrasound probe). In another example, repolarization may be complete in response to a user requesting conclusion of repolarization and/or requesting execution of a next imaging sequence. In yet another example, repolarization may be complete after a set duration of executing the repolarization sequence. In still another example, repolarization may be automatically determined to be complete (and automatically stopped) after the sensitivity of the probe increases above a second threshold (which may be higher than the threshold at 412). If it is determined at 420 that repolarization is not complete, the method continues to 422 to continue applying the repolarization sequence to the probe. The method then loops back to 420. Alternatively, if it is determined that repolarization is complete at 420, the method proceeds to 424 to initiate the next imaging sequence, similar to the method at 408.

At 426, the method includes, after completion of the final imaging sequence (e.g., the last requested or programmed imaging sequence), stopping imaging (stopping sending imaging transmit pulses to the probe) and applying one or more repolarization sequences to the probe if requested. For example, a user may request that repolarization occurs after conclusion of imaging. In another embodiment, applying a repolarization sequence to the probe may occur automatically after conclusion of a final imaging sequence. The method then ends.

In this way, by utilizing the real-time repolarization sequence and method described above, it may be possible to increase the transmit voltage of the imaging transmit pulses in the imaging mode (which potentially depolarize transducers easily without real-time repolarization). This may increase the penetration of the ultrasound waves emitted from the probe in the imaging mode, thereby resulting in increased image quality and more accurate diagnosis based on the generated image.

Figure 5:
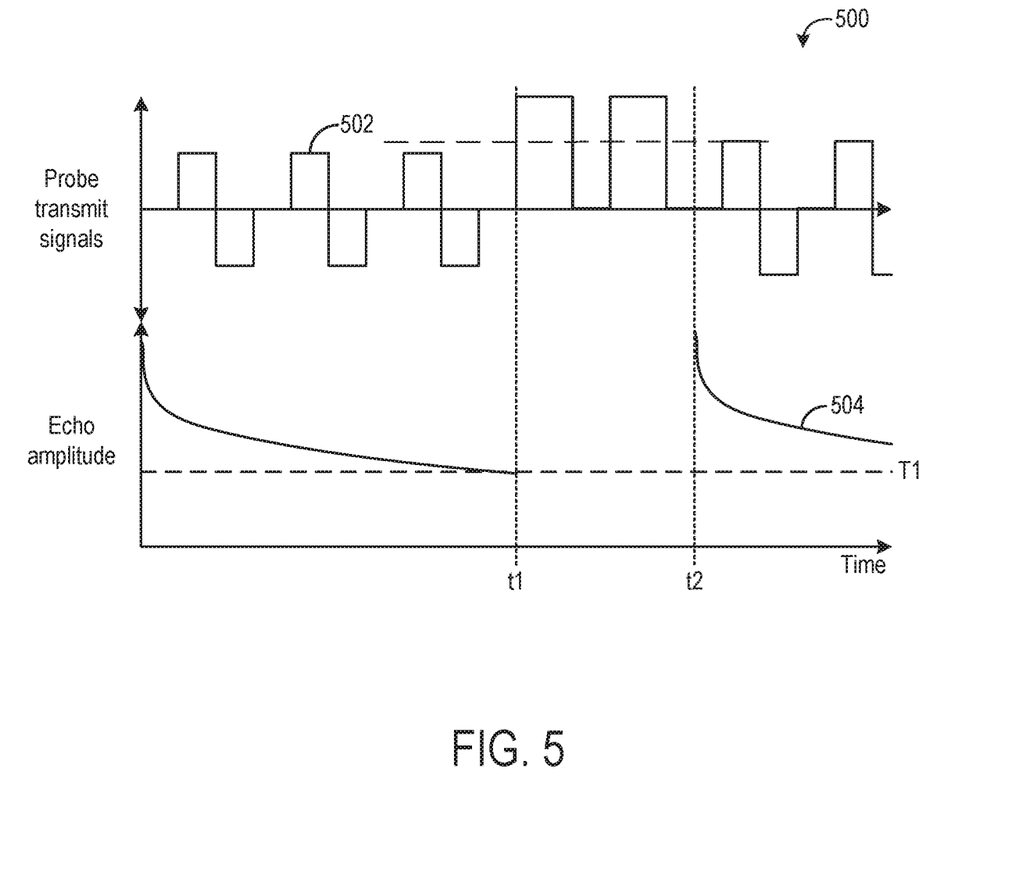
FIG. 5 shows an example graph of changes in sensitivity of an ultrasound probe during imaging, according to an embodiment of the invention.

FIG. 5 shows an example graph 500 of changes in sensitivity of an ultrasound probe during imaging. Specifically, graph 500 shows transmit signals (pulses) applied to transducer elements of the ultrasound probe at plot 502 and changes in echo amplitude (which may correlate to a sensitivity level of the probe) of received echo signals at the probe over time at plot 504. Prior to time t1, an imaging sequence is being executed and a plurality of imaging transmit pulses are sent to the elements of the probe. In this example, the pulses are bipolar pulses. During execution of the imaging sequence, the amplitude of the received echo signals gradually decreases until, at time t1, the echo amplitude reaches the threshold sensitivity level T1. In response to the echo amplitude of the received echo signals reaching and/or falling below the threshold sensitivity level T1, the probe transmit signals are transitioned from applying imaging transmit pulses to applying repolarization transmit pulses of a repolarization sequence. In this way, between times t1 and t2, imaging with the probe is stopped and repolarization of the probe is executed. In this example, the repolarization sequence includes unipolar pulses with a positive polarity. After a set repolarization duration, the repolarization ends and next imaging sequence is applied to the probe. As can be seen at time t2, the sensitivity of the probe returns to a higher level after execution the repolarization sequence. Further, due to applying the repolarization sequence to the probe between imaging sequences, a voltage (e.g., amplitude) of the imaging transmit pulses of the imaging sequence applied to the probe after time t2 may be increased. This may result in a higher image quality.

In this way, applying a repolarization sequence to transducer elements of an ultrasound probe either before, after, or interleaved between imaging sequences may maintain and/or increase the sensitivity of the ultrasound probe. Specifically, a repolarization sequence may include one or more repolarization transmit signals that have an average polarity that is in a same direction as the polarity of the ferroelectric material of the ultrasound transducer elements. Thus, after applying a repolarization sequence to the probe, the dipoles of the material of the transducer elements may become realigned and thus the probe may be repolarized. As a result, the sensitivity of the probe may be increased and a resulting imaging quality of an image generated from subsequent imaging sequences may be increased. Further, applying the repolarization sequences at regular intervals, or based on a sensitivity of the probe (determined in real-time during applying imaging sequences to the probe), may decrease a rate or likelihood of depolarization of the transducer elements. As a result, a higher voltage may be applied to the probe during imaging (e.g., the voltage (or amplitude) of the imaging transmit pulses may be increased), thereby allowing for a deeper penetration into the imaged object due to increased acoustic energy and, thus, a higher quality and more accurate ultrasound image of the imaged object. The technical effect of executing one or more imaging sequences with an ultrasound transducer; and applying a repolarization sequence to the ultrasound transducer one or more of before, after, and interleaved between the one or more imaging sequences, where the repolarization sequence is separate from the one or more imaging sequences, is to obtain an image with increased image quality by increasing the sensitivity and pulse voltage amplitude of the probe.

As one embodiment, a method comprises: executing one or more imaging sequences with an ultrasound transducer; and applying a repolarization sequence to the ultrasound transducer one or more of before, after, and interleaved between the one or more imaging sequences, where the repolarization sequence is separate from the one or more imaging sequences. In one example of the method, executing the one or more imaging sequences includes sending a sequence of imaging transmit signals adapted for imaging to transducer elements of the ultrasound transducer. In another example of the method, applying the repolarization sequence includes sending one or more repolarization transmit signals adapted for repolarization of the ultrasound transducer to transducer elements of the ultrasound transducer, where the repolarization transmit signals are different than and separate from the imaging transmit signals. In yet another example of the method, applying the repolarization sequence includes applying one of a unipolar or multipolar repolarization sequence where an average polarity of the repolarization sequence is in a same direction as a polarity of dipoles of a ferroelectric material of transducer elements of the ultrasound transducer. In another example of the method, applying the repolarization sequence is responsive to a received user input and occurs one of prior to executing the one or more imaging sequences, after executing the one or more imaging sequences, or interleaved between sequences of the one or more imaging sequences. In still another example of the method, applying the repolarization sequence occurs automatically after and in response to a set, threshold number of imaging pulses of the one or more imaging sequences being executed. In one example, applying the repolarization sequence includes applying a number of repolarization pulses and wherein the number of repolarization pulses is less than the threshold number of imaging pulses. The method may further comprise, determining a sensitivity level of the ultrasound probe during the executing the one or more imaging sequences and where applying the repolarization sequence occurs automatically, in response to the determined sensitivity level decreasing to a threshold sensitivity level. In one example, applying the repolarization sequence occurs after a conclusion of an imaging sequence of the one or more imaging sequences that is occurring while the sensitivity level of the ultrasound probe is determined to be at or below the threshold sensitivity level and before executing a subsequent imaging sequence of the one or more imaging sequences. In another example, the determined sensitivity level is based on an amplitude of echoes received by the ultrasound transducer during executing the one or more imaging sequences. In another example of the method, applying the repolarization sequence occurs while displaying an image generated from echo signals received from executing the one or more imaging sequences.

As another embodiment, a method comprises: executing an imaging sequence by applying one or more imaging transmit pulses adapted for imaging to an ultrasound transducer; determining a sensitivity of the ultrasound transducer during executing the imaging sequence; and in response to the determined sensitivity decreasing to a threshold level, applying a repolarization sequence to the ultrasound transducer following a conclusion of the executed imaging sequence. In one example of the method, applying the repolarization sequence includes applying one or more repolarization transmit pulses adapted for repolarization to the ultrasound transducer, where the repolarization transmit pulses and different than and occur separately from the one or more imaging transmit pulses. In another example of the method, the one or more imaging transmit pulses includes a first number of imaging transmit pulses and wherein applying the repolarization sequence includes applying a second number of repolarization transmit pulses to the ultrasound transducer, the second number less than the first number. In one example, the second number is determined automatically as a function of the first number. In another example, the second number is determined responsive to the sensitivity of the ultrasound transducer.

As yet another embodiment, an ultrasound system comprises: an ultrasound probe including an array of transducer elements; and a transmit beamformer having transmit channels coupled to the transducer elements; and a controller with computer readable instructions stored on non-transitory memory that when executed during operation of the ultrasound system, cause the controller to: apply one or more sequences of imaging transmit signals via the transmit beamformer to the ultrasound probe; and apply one or more sequences of repolarization transmit signals via the transmit beamformer to the ultrasound probe one or more of before, after, or interleaved between the one or more sequences of imaging transmit signals. In one example of the system, the imaging transmit signals are different than and separate from the repolarization transmit signals and wherein an amplitude of the repolarization transmit signals is greater than an amplitude of the imaging transmit signals. In another example of the system, the imaging transmit signals include one of a b-mode pulse signal and a harmonic pulse signal. In yet another example of the system, the transducer elements comprise a ferroelectric material and wherein the repolarization transmit signals are one of unipolar or multipolar with an average polarity being in a direction of dipoles of the ferroelectric material. The system may further comprise a display device and wherein the computer readable instructions further cause the controller to: generate an image from echo signals received as a result of applying the one or more sequences of imaging transmit signals; and display the generated image during applying the one or more sequences of repolarization transmit signals.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    executing one or more imaging sequences with an ultrasound transducer; and
    applying a repolarization sequence to the ultrasound transducer one or more of before, after, and interleaved between the one or more imaging sequences, where the repolarization sequence is separate from the one or more imaging sequences, wherein applying the repolarization sequence occurs while displaying an image generated from echo signals received from executing the one or more imaging sequences.

2. The method of claim 1, wherein executing the one or more imaging sequences includes sending a sequence of imaging transmit signals adapted for imaging to transducer elements of the ultrasound transducer.

3. The method of claim 2, wherein applying the repolarization sequence includes sending one or more repolarization transmit signals adapted for repolarization of the ultrasound transducer to transducer elements of the ultrasound transducer, where the repolarization transmit signals are different than and separate from the imaging transmit signals.

4. The method of claim 1, wherein applying the repolarization sequence includes applying one of a unipolar or multipolar repolarization sequence where an average polarity of the repolarization sequence is in a same direction as a polarity of dipoles of a ferroelectric material of transducer elements of the ultrasound transducer.

5. The method of claim 1, wherein applying the repolarization sequence is responsive to a received user input and occurs one of prior to executing the one or more imaging sequences, after executing the one or more imaging sequences, or interleaved between sequences of the one or more imaging sequences.

6. The method of claim 1, wherein applying the repolarization sequence occurs automatically after and in response to a set, threshold number of imaging pulses of the one or more imaging sequences being executed, wherein applying the repolarization sequence includes applying a number of repolarization pulses, and wherein the number of repolarization pulses is less than the threshold number of imaging pulses.

7. The method of claim 1, further comprising determining a sensitivity level of the ultrasound probe during the executing the one or more imaging sequences and wherein applying the repolarization sequence occurs automatically, in response to the determined sensitivity level decreasing to a threshold sensitivity level.

8. The method of claim 7, wherein applying the repolarization sequence occurs after a conclusion of an imaging sequence of the one or more imaging sequences that is occurring while the sensitivity level of the ultrasound probe is determined to be at or below the threshold sensitivity level and before executing a subsequent imaging sequence of the one or more imaging sequences.

9. The method of claim 7, wherein the determined sensitivity level is based on an amplitude of echoes received by the ultrasound transducer during executing the one or more imaging sequences.

10. An ultrasound system, comprising:
    an ultrasound probe including an array of transducer elements; and
    a transmit beamformer having transmit channels coupled to the transducer elements;
    a display device; and
    a controller with computer readable instructions stored on non-transitory memory that when executed during operation of the ultrasound system, cause the controller to:
        apply one or more sequences of imaging transmit signals via the transmit beamformer to the ultrasound probe;
        generate an image from echo signals received as a result of applying the one or more sequences of imaging transmit signals;
        apply one or more sequences of repolarization transmit signals via the transmit beamformer to the ultrasound probe one or more of before, after, or interleaved between the one or more sequences of imaging transmit signals; and
        display the generated image during applying the one or more sequences of repolarization transmit signals.

11. The ultrasound system of claim 10, wherein the imaging transmit signals are different than and separate from the repolarization transmit signals and wherein an amplitude of the repolarization transmit signals is greater than an amplitude of the imaging transmit signals.

12. The ultrasound system of claim 10, wherein the imaging transmit signals include one of a b-mode pulse signal and a harmonic pulse signal.

13. The ultrasound system of claim 10, wherein the transducer elements comprise a ferroelectric material and wherein the repolarization transmit signals are one of unipolar or multipolar with an average polarity being in a direction of dipoles of the ferroelectric material.

14. A method, comprising:
    executing one or more imaging sequences with an ultrasound transducer;
    determining a sensitivity level of the ultrasound probe during the executing of the one or more imaging sequences; and
    applying a repolarization sequence to the ultrasound transducer one or more of before, after, and interleaved between the one or more imaging sequences, where the repolarization sequence is separate from the one or more imaging sequences, wherein applying the repolarization sequence occurs automatically in response to the determined sensitivity level decreasing to a threshold sensitivity level.

15. A method, comprising:
    executing one or more imaging sequences with an ultrasound transducer;

determining an image quality degradation of an image generated from echo signals received as a result of executing the one or more imaging sequences; and applying a repolarization sequence to the ultrasound transducer one or more of before, after, and interleaved between the one or more imaging sequences, where the repolarization sequence is separate from the one or more imaging sequences, wherein applying the repolarization sequence occurs automatically in response to the determined image quality degradation.

* * * * *